(12) United States Patent
Deinhammer et al.

(10) Patent No.: US 8,076,112 B2
(45) Date of Patent: Dec. 13, 2011

(54) FERMENTATION PROCESSES

(75) Inventors: Randy Deinhammer, Wake Forest, NC (US); Rikke Monica Festersen, Herlev (DK)

(73) Assignee: Novozymes A/S, Bagsvaerd (DK)

( * ) Notice: Subject to any disclaimer, the term of this patent is extended or adjusted under 35 U.S.C. 154(b) by 320 days.

(21) Appl. No.: 12/282,732

(22) PCT Filed: Mar. 22, 2007

(86) PCT No.: PCT/US2007/064592
§ 371 (c)(1),
(2), (4) Date: Sep. 12, 2008

(87) PCT Pub. No.: WO2007/109750
PCT Pub. Date: Sep. 27, 2007

(65) Prior Publication Data
US 2009/0098624 A1 Apr. 16, 2009

Related U.S. Application Data

(60) Provisional application No. 60/784,777, filed on Mar. 22, 2006.

(51) Int. Cl.
*C12P 7/06* (2006.01)

(52) U.S. Cl. .................................................. 435/161
(58) Field of Classification Search .................. None
See application file for complete search history.

(56) References Cited

U.S. PATENT DOCUMENTS

2004/0023349 A1  2/2004  Bisgaard-Frantzen et al.

OTHER PUBLICATIONS

Narendranath, N. V., "Bacterial contamination and control in ethanol production" 2003, Chapter 20, The alcohol Text book, 4th edition, p. 287-298.*
Mygind et al. ,Nature, 2005, vol. 437, p. 975-980.*
Lee et al., Biotechnology and Bioengineering, 1983, vol. XXV, p. 659-669.*
Bayrock et al., Abstract, Appl. Microbiol. Biotechnoll, vol. 62, pp. 498-502 (2003).
Maiesetta et al., Abstract & p. 3350, Antimicrobial Agents & Chemotherapy, vol. 47, No. 10, pp. 3349-3351 (2003).
Narendranath et al., Abstract & p. 4158, vol. 63, No. 11, pp. 4158-4161 (1997).

* cited by examiner

*Primary Examiner* — Kade Ariani
(74) *Attorney, Agent, or Firm* — Elias Lambiris

(57) ABSTRACT

The present invention provides a fermentation process for producing a fermentation product from starch-containing material wherein one or more antibacterial agents are added before and/or during fermentation.

21 Claims, 4 Drawing Sheets

FERMENTATION PROCESSES

CROSS-REFERENCE TO RELATED APPLICATIONS

This application is a 35 U.S.C. 371 national application of PCT/US2007/064592 filed Mar. 22, 2007, which claims priority or the benefit of U.S. provisional application No. 60/784,777 filed Mar. 22, 2006, the contents of which are fully incorporated herein by reference.

FIELD OF THE INVENTION

The present invention relates to processes for producing fermentation products from starch-containing material, including processes for producing ethanol.

BACKGROUND OF THE INVENTION

Fermentation processes are used for making a vast number of commercial products, including alcohols (e.g. ethanol, methanol, butanol, 1,3-propanediol); organic acids (e.g., citric acid, acetic acid, itaconic acid, gluconic acid, gluconate, lactic acid, succinic acid, 2,5-diketo-D-gluconic acid; ketones (e.g., acetone); amino acids (e.g. glutamic acid); gases (e.g., $H_2$ and $CO_2$), and more complex compounds, including, for example, antibiotics (e.g., penicillin and tetracycline); enzymes; vitamins (e.g., riboflavin, $B_{12}$, beta-carotene); hormones, and other compounds which are difficult to produce synthetically. Fermentation processes are also commonly used in dairy (e.g., in the production of yogurt and cheese), leather, and tobacco industries.

Fermentation products are produced industrially in large fermentation tanks capable of holding upwards of 10 cubic meters fermentation medium. In order to build up a suitable fermenting organism population and concentration in the fermentation tank a fermentation process usually requires a process time of between 48 and 120 hours or more. Because of the large-sized tanks and long fermentation times it is difficult to maintain the fermentation system free of contamination. Unwanted contaminant bacteria are often gram-positive bacteria from the genus *Lactobacillus* that converts glucose into lactic acid and acetic acid. Also gram-negative bacteria are known to contaminate fermentation processes. Unfortunately the fermentation conditions are usually conducive for bacterial growth. If bacterial contamination occurs the entire fermentation tank must be emptied, cleaned and sterilized and the fermentation medium is useless. This is of course time-consuming and costly. Further, many bacteria compete with the fermenting organism for the sugar. This results in a reduced fermentation yield.

Bayrock et al., 2003, Appln. Microbiol. Biotechnol. 62:498-502 disclose control of *Lactobacillus* contaminants in continuous fuel ethanol fermentations by constant or pulse addition of penicillin G.

Today antibiotics, heat and chemical disinfectants are used for killing and/or inhibiting growth of unwanted bacteria. These disinfectants are added to the fermentation before or during fermentation, The known antibacterial agents including antibiotics, such as penicillin, are sometimes not desired. Therefore, there is a need for further means for killing and/or inhibiting unwanted bacteria growth during fermentation processes.

SUMMARY OF THE INVENTION

The object of the present invention is to provide fermentation processes, or processes including a fermentation step, wherein unwanted bacteria are killed and/or unwanted bacteria growth is inhibited.

In the first aspect the present invention provides processes for producing a fermentation product from starch-containing material using a fermenting organism, wherein one or more antibacterial agents are added before and/or during fermentation.

In the second aspect the invention relates to a process for producing a fermentation product from starch-containing material comprising the steps of:
(a) liquefying starch-containing material;
(b) saccharifying using a carbohydrate source generating enzyme;
(c) fermenting using a fermenting organism,
wherein one or more antibacterial agents are added before and/or during fermentation.

In the third aspect the invention relates to a process for producing a fermentation product from starch-containing material comprising:
(a) saccharifying starch-containing material at a temperature below the initial gelatinization temperature of said starch-containing material,
(b) fermenting using a fermenting organism,
wherein one or more antibacterial agents are added before and/or during fermentation.

Finally the invention also relates to use of antibacterial agents for killing and/or inhibiting bacterial growth in fermentation product production processes.

DEFINITIONS

The term "antibacterial activity" means activity which is capable of killing and/or inhibiting growth of bacteria. An "antibacterial peptide" is a peptide capable of killing and/or inhibiting growth of bacteria. In a similar manner an "antibacterial polypeptide" and "antibacterial enzyme: are polypeptides and enzymes, respectively, capable of killing and/or inhibiting growth of bacteria. In the context of the present invention the term "inhibiting growth of microbial bacteria" is intended to mean that the bacteria are in the non-growing state, i.e., that they are not able to multiplicate. It is to be understood that an "antibacterial peptide" or the like may also be capable of killing and/or inhibiting growth of other microbial cells, such as certain fungal cells.

When used herein, a "fragment" of an amino acid sequence, peptide, polypeptide, enzyme etc. means a subsequence wherein one or more amino acids have been deleted from the amino and/or carboxyl terminus. Preferably one or more amino acids have been deleted from the carboxyl terminus. A fragment should also have antibacterial activity.

An antimicrobial peptide, polypeptide, protein, enzyme or the like used in a process of the invention may be a "variant" which comprises, preferably consists of, an amino acid sequence that has at least one substitution, deletion and/or insertion of an amino acid as compared to the parent/wild-type amino acid sequence. Such variant may be constructed by any technique known in the art, such as by site-directed/random mutagenesis and domain shuffling techniques. In one embodiment the amino acid change(s) (in the variant as well as in parent/wild-type sequence) is(are) of minor nature, such as conservative amino acid substitution(s), that do not significantly affect the folding and/or activity of the molecule.

The term "homology" between two amino acid sequences or between two nucleotide sequences is described by the parameter "identity".

The degree of "identity" between two amino acid sequences is determined by using the program FASTA included in version 2.0x of the FASTA program package (see W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA", Methods in Enzymology 183: 63-98). The scoring matrix used was BLOSUM50, gap penalty was −12, and gap extension penalty was −2.

The degree of identity between two nucleotide sequences is determined using the same algorithm and software package as described above. The scoring matrix used was the identity matrix, gap penalty was −16, and gap extension penalty was −4.

The term "unwanted bacteria" means in context of the invention bacteria that is undesired in that they may impact fermentation product production in a negative way, for instance, by converting the fermenting organism's substrate into an undesired fermentation product. An example of unwanted contaminant bacteria in, e.g., alcohol production, including ethanol production, is *Lactobacillus* that converts glucose into lactic acid and acetic acid.

DESCRIPTION OF THE INVENTION

Figure 1:
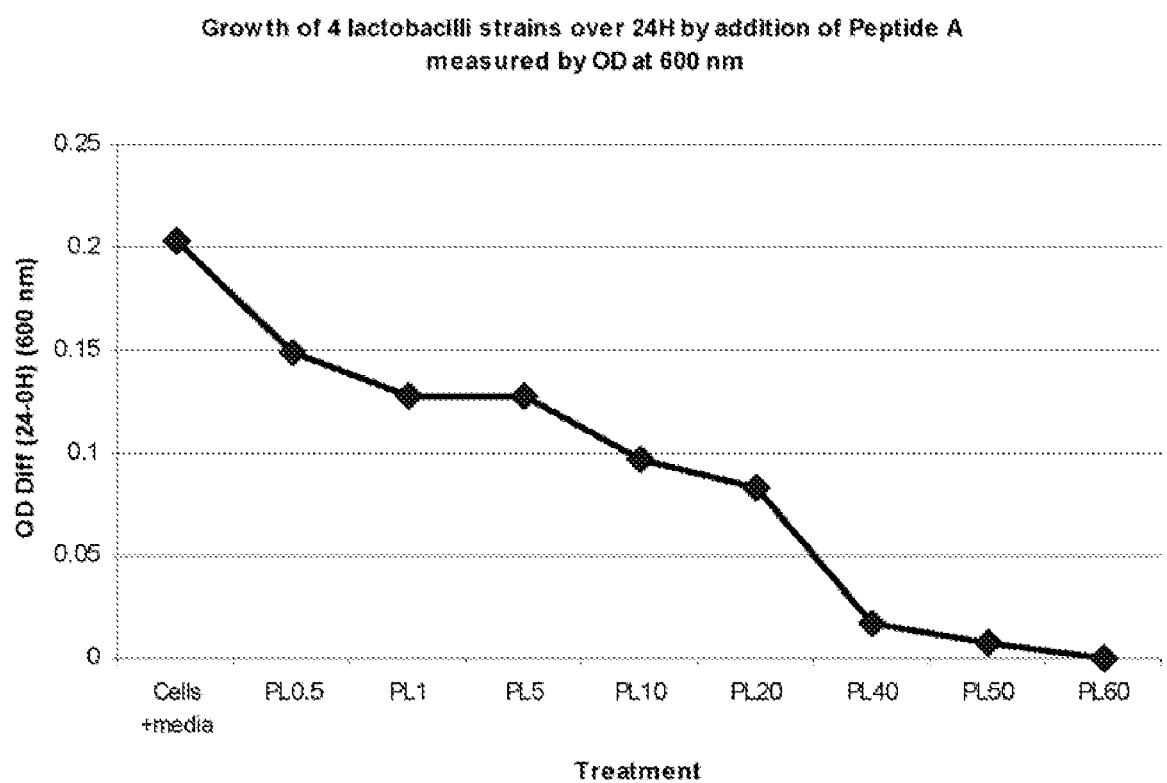
FIG. 1 shows the growth of mixture of four *Lactobacillus* strains over 24 hours at different concentrations of antibacterial Peptide A.

The object of the present invention is to provide fermentation processes or processes including a fermentation step wherein unwanted bacteria are killed and/or unwanted bacteria growth is inhibited. Unwanted bacteria themselves and their metabolic end-products, such as lactic acid and/or acetic acid, lead to reduced fermentation yields which lead to considerable economical loss to the producer (see Thomas et al., 2001, J. Applied Microbiology, 90: 819-828). The unwanted bacteria compete with the fermenting organism (e.g., yeast) for sugar (carbon source) in the fermentation medium. The lactic acid and/or acetic acid produced by the unwanted bacteria may also have a negative impact on yeast growth.

The present inventors have found that antibacterial agents may advantageously be used to kill and/or inhibit growth of unwanted bacteria which are known to contaminate fermentation processes. A process of the invention may be used as an alternative to, e.g., adding antibiotics, such as especially penicillin, to fermentation processes, which may be undesired for one reason or another. A process of the invention may result in a fermentation yield that is increased compared to the yield obtained in a corresponding process where no antibacterial agent is added.

According to the invention especially bacterial contamination by lactic acid and/or acetic acid producing bacteria may be prevented and/or reduced. Lactic acid and/or acetic acid producing bacteria of especially the genus *Lactobacillus* are known to contaminate fermentation processes. Examples of species of *Lactobacillus* that has been found to contaminate fermentation processes include strains of *Lactobacillus collinoides, Lactobacillus brevis, Lactobacillus fermentum, Lactobacillus paracasei, Lactobacillus plantarum*, and/or *Lactobacillus rhamnosus*, or a mixture thereof.

Processes of the Invention

In the first aspect the invention relates to processes for producing a fermentation product from starch-containing material using a fermenting organism, wherein one or more antibacterial agents are added before and/or during fermentation.

A fermentation process of the invention includes, without limitation, fermentation processes used to produce fermentation products including alcohols (e.g., ethanol, methanol, butanol, 1,3-propanediol); organic acids (e.g., citric acid, acetic acid, itaconic acid, gluconic acid, gluconate, lactic acid, succinic acid, 2,5 diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline), enzymes; vitamins (e.g., riboflavin, $B_{12}$, beta-carotene); hormones, and other compounds. Fermentation processes also include fermentation processes used in dairy industry (e.g., fermented dairy products), leather industry and tobacco industry. Preferred fermentation processes include alcohol fermentation processes, which are well known in the art. Preferred fermentation processes are anaerobic fermentation processes. In an embodiment the fermentation process of the invention is part of a process further comprises a liquefaction step and/or a saccharification step. In a preferred embodiment the fermentation process is a step in a simultaneous saccharification and fermentation process (SSF process) or a one-step fermentation process of uncooked starch-containing material (sometimes referred to as simultaneous liquefaction, saccharification and fermentation (LSF)). Examples of one-step processes include the processes disclosed in U.S. Pat. No. 4,316,956; US 2004/0234649 and WO 2003/066816 and WO 2003.066826 (which references are all incorporated by reference).

The fermentation process of the invention may in one embodiment be carried out at a temperature in the range from 20-40° C., preferably 30-35° C., especially around 32° C. This is usually the case when producing alcoholic fermentation products such as ethanol, especially fuel ethanol, potable ethanol and/or industrial ethanol.

The pH during fermentation may in a preferred embodiment be in the range between 4-7, preferably in the range between 5 and 6.

In one embodiment the antibacterial agent is added during liquefaction and/or saccharification, i.e., before fermentation, or during simultaneous saccharification and fermentation (SSF). In another embodiment the antibacterial agent is added to backset and/or thin stillage recycled to typically the liquefaction and/or fermentation steps.

Fermentation processes are usually carried out as batch fermentation, i.e., fermentation conducted from start to finish in a single tank, or continuous fermentation, i.e., a steady state fermentation system that operates without interruption and where each stage of fermentation occurs in a separate section of the fermentation system, and flow rates are set to correspond to required residence times. In other words, the individual process steps in a process comprising a fermentation process of the invention may be performed batch wise or continuously. Processes where all process steps are performed batch wise, or processes where all process steps are performed continuously, or processes where one or more process steps are performed batch wise and one or more process steps are performed continuously are contemplated according to the invention. The cascade process is an example of a process where one or more process steps are performed continuously and as such contemplated for the invention. For further information on the cascade process and other especially ethanol processes consult "The Alcohol Textbook", Ethanol production by fermentation and distillation. Eds. T. P. Lyons, D. R. Kesall and J. E. Murtagh. Nottingham University Press 1995. In a preferred embodiment the fermentation process of the invention is part of a continuous fermentation product production process.

In a preferred embodiment the antibacterial agent is left in contact with the fermentation medium for between 1 minute and 48 hours, preferably at least 1 hour, especially at least 24 hours before inoculation of the fermenting organism.

A process of the invention may be carried out for a period of 1 to 250 hours, preferably from 25 to 190 hours, more preferably from 30 to 180 hours, more preferably from 40 to 170 hours, even more preferably from 50 to 160 hours, yet more preferably from 60 to 150 hours, even yet more preferably from 70 to 140 hours, and most preferably from 80 to 130 hours.

Fermentation Medium

"Fermentation media", "fermentation medium" or 'fermentation broth' refers to the environment in which fermentation is carried out and which includes the fermentation substrate, that is, the carbohydrate source that is metabolized by the fermenting organism. The fermentation medium, including fermentation substrate and other raw materials used in the fermentation process of the invention may be processed, e.g., by milling, liquefaction and/or saccharification or other desired steps prior to or simultaneously with the fermentation process. Accordingly, the fermentation medium can refer to the medium before the fermenting organism is added, such as, the medium in or resulting from liquefaction and/or saccharification, as well as the medium which comprises the fermenting organism, such as, the medium used in simultaneous saccharification and fermentation processes (SSF) or one-step fermentation (LSF) of, e.g. uncooked raw material.

Fermenting Organisms

"Fermenting organism" refers to any organism suitable for use in a desired fermentation process. Suitable fermenting organisms according to the invention are able to ferment, i.e., convert, sugars, such as glucose or maltose, directly or indirectly into a desired fermentation product. Examples of fermenting organisms include fungal organisms, such as especially yeast. Preferred yeast includes strains of *Saccharomyces* spp., and in particular, strains of *Saccharomyces cerevisiae*. Commercially available yeast includes, e.g., ETHANOL RED™ yeast (available from Fermentis/Lesaffre, USA), FALI (available from Fleischmann's Yeast, USA), SUPERSTART™ and THERMOSACC® fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

Starch-Containing Materials

Any suitable starch-containing material, including granular starch, may be used as substrate according to the present invention, The material is generally selected based on the desired fermentation product. Examples of starch-containing materials suitable for use in a process of present invention include tubers, roots, stems, whole grains, corn, cob, wheat, barley, rye, milo, sago, cassaya, tapioca, sorghum, sweet sorghum, rice peas, beans, or sweet potatoes, or mixtures thereof, or cereals, sugar-containing raw materials, such as molasses, fruit materials, sugar cane or sugar beet, potatoes, and cellulose-containing materials, such as wood or plant residues, or mixtures thereof. Contemplated are both waxy and non-waxy types of corn and barley.

Suitable substrates also include carbohydrate sources, in particular, low molecular sugars $DP_{1-3}$ that can be metabolized by the fermenting organism, and which may be supplied by direct addition to the fermentation medium.

Antibacterial Agents

An antibacterial agent used in a process of the invention is preferably a polymer molecule, such as a polymer molecule consisting of an amino acid sequence. The amino acid sequence may be a peptide, polypeptide, protein or enzyme or the like.

In a preferred embodiment the antibacterial agent is a peptide, polypeptide, protein, enzyme or the like capable of killing and/or inhibiting growth of unwanted bacteria, preferably gram positive bacteria and/or gram negative bacteria, especially gram positive bacteria of the genus *Lactobacillus*.

The antibacterial peptide, polypeptide, protein, enzyme or the like may be of microbial, such as fungal or bacterial origin, but may also be synthetically produced.

In a preferred embodiment the antibacterial agent is a defensin or defensin-like peptide. In a preferred embodiment the antibacterial peptide is a fungal defensin, preferably derivable from *Pseudoplectania nigrella*, especially *Pseudoplectania nigrella* CBS 444.97. Specifically contemplated is the peptide disclosed as amino acids 1-40 in SEQ ID NO: 2 in WO 2003/044049 (which is hereby incorporated by reference) or a fragment thereof having antibacterial activity or a variant therefore having antibacterial activity having at least 80%, preferably at least 90%, more preferably at least 95%, even more preferably at least 97%, especially at least 99% identity to amino acids 1-40 in SEQ ID NO; 2 in WO 2003/044049.

In a specific embodiment the antibacterial agent is the peptide Novispirin or a Novispirin variant selected from the group disclosed as SEQ ID NOS: 1-37 in WO 2002/00839, especially G10 disclosed as SEQ ID NO: 17 in WO 2002/00839 (which is incorporated by reference). In a preferred embodiment the antibacterial peptide is a variant of Novispirin G10 (SEQ ID NO: 1 in WO 2005/105831). Contemplated variants include any of the variants disclosed as SEQ ID NOS: 2-116 in WO 2005/105831.

In another preferred embodiment the antibacterial agent is an antibacterial protein or enzyme such as Lysozyme. Lysozyme may be of any origin, such as hen Lysozyme.

The antibacterial agent(s) is(are) added in concentrations sufficient to kill and/or inhibit growth of bacteria cells, preferably gram positive bacteria and/or gram negative bacteria cells, especially gram positive bacteria cells of the genus *Lactobacillus*, including *Lactobacillus brevis, Lactobacillus collinoides, Lactobacillus fermentum, Lactobacillus paracasei, Lactobacillus plantarum*, and/or *Lactobacillus rhamnosus*, or mixtures of one or more thereof.

Other contemplated antimicrobial peptides includes: Heliomicin (antifungal acting AMP disclosed in WO 1999/053053), Eurocin (WO 2006/050737); Piceasin, Oystrisin, Virgisin, and Gibbosin (WO 2006/053565); Marinasin (WO 2006/097110). Other examples of antimicrobial agents include the antifungal peptide disclosed in WO 2002/090384. All references are hereby incorporated in their full length.

According to the invention the antibacterial agent(s) is(are) added in a concentration between 0.1-1000 mg/L fermentation medium, preferably between 0.5-500 mg/L fermentation medium, especially between 1-100 mg/L fermentation medium.

Producing Fermentation Products from Gelatinized Starch-Containing Material

In this aspect the present invention relates to a process for producing a fermentation product, especially ethanol, from starch-containing material, which process includes a liquefaction step and separately/sequentially or simultaneously performed saccharification and fermentation steps.

Therefore, in this aspect the invention relates to a process for producing a fermentation product from starch-containing material comprising the steps of:

(a) liquefying starch-containing material;
(b) saccharifying using a carbohydrate-source generating enzyme;
(c) fermenting using a fermenting organism,
wherein one or more antibacterial agents are added before and/or during fermentation.

The fermentation product, such as especially ethanol, may optionally be recovered after fermentation, e.g., by distillation. The fermentation step (c) may be a fermentation process of the invention as described herein. Suitable starch-containing starting materials are listed in the section "Starch-Containing Materials"-section above. In a preferred embodiment liquefaction step (a) is performed using an alpha-amylase. Contemplated enzymes and suitable concentrations are listed in the "Enzymes"-section below. Fermentation is preferably carried out in the presence of yeast, preferably a strain of *Saccharomyces*. Suitable fermenting organisms are listed in the "Fermenting Organisms"-section above. Examples of suitable antibacterial agents are listed in the section "Antibacterial Agents" above.

The antibacterial agent may also be added during liquefaction and/or saccharification, i.e., before initiation of fermentation. Alternatively the antibacterial agent may be added to the backset and/or thin stillage recycled to, e.g., the liquefaction and/or fermentation steps. In a preferred embodiment the antibacterial agent is left in contact with the fermentation medium for at least between 1 minute and 48 hours, preferably at least 1 hour, especially at least 24 hours before inoculation of the fermenting organism.

Liquefaction is carried out by heating to above the gelatinization temperature of the starch-containing material.

In a preferred embodiment step (b) and (c) are carried out simultaneously (SSF process).

In a particular embodiment, the process of the invention further comprises, prior to step (a), the steps of:

x) reducing the particle size of the starch-containing material, preferably by milling;
y) forming a slurry comprising starch-containing material and water.

The slurry may include water and/or process waters, such as backset and/or thin stillage, scrubber water, evaporator condensate or distillate, side stripper water from distillation, or other fermentation product plant process water. In a preferred embodiment the starch-containing material is reduced in size by either dry milling or wet milling. However, other size reducing technologies such as emulsifying technology, rotary pulsation may also be used. The aqueous slurry may contain from 10-40 wt-%, preferably 25-35 wt-% starch-containing material. The slurry is heated to above the gelatinization temperature and alpha-amylase, preferably bacterial and/or acid fungal alpha-amylase may be added to initiate liquefaction (thinning). The slurry may in an embodiment be jet-cooked to further gelatinize the slurry before being subjected to an alpha-amylase in step (a). However, it is to be understood that liquefaction may be carried out without a jet-cooking step.

More specifically liquefaction may be carried out as a three-step hot slurry process, The slurry is heated to between 60-95° C., preferably 80-85° C., and alpha-amylase is added to initiate liquefaction (thinning). Then the slurry may be jet-cooked at a temperature between 95-140° C. preferably 105-125° C., for 1-15 minutes, preferably for 3-10 minutes, especially around 5 minutes, The slurry is cooled to 60-95° C. and more alpha-amylase is added to finalize hydrolysis (secondary liquefaction), The liquefaction process may be carried out at pH 4.5-6.5, in particular at a pH between 5 and 6. Milled and liquefied whole grains are known as mash.

The saccharification step (b) may be carried out using conditions well known in the art. For instance, a full saccharification process may last up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation process (SSF process). Saccharification is typically carried out at temperatures from 30-65° C., typically around 60° C., and at a pH between 4 and 5, normally at about pH 4.5.

The most widely used process in fermentation product production processes, especially ethanol production, is simultaneous saccharification and fermentation (SSF), in which there is no holding stage for the saccharification, meaning that the fermenting organism, such as yeast, and enzyme(s) may be added together. SSF may be carried out at a temperature in the range from 20-40° C., preferably 30-35° C., especially around 32° C. The pH during SSF is typically in the range between 4 and 7, preferably between 5 and 6.

Producing Fermentation Products from Un-Gelatinized/Uncooked Starch-Containing Material.

Especially in one-step fermentation processes using uncooked starch-containing material as the starting material adding antibacterial agents are advantageous as one-step fermentation processes are performed at low temperatures in the range below 20-40° C. For instance, one-step ethanol fermentation processes of the invention are typically carried out at around 32° C. using *Saccharomyces cerevisiae* as the fermenting organism.

Therefore, in this aspect of the invention relates to a process for producing a fermentation product from starch-containing material comprising:

(a) saccharifying starch-containing material at a temperature below the initial gelatinization temperature of said starch-containing material,
(b) fermenting using a fermenting organism,
wherein one or more antibacterial agents are added before and/or during fermentation.

The fermentation product, such as especially ethanol, may optionally be recovered after fermentation, e.g., by distillation. The fermentation step (b) may be a fermentation process of the invention as described herein. Suitable starch-containing starting materials are listed in the section "Starch-Containing Materials"-section above. In a preferred embodiment the starch-containing material is granular starch. Saccharification step (a) and fermentation step (b) may be carried out sequentially or simultaneously. In a preferred embodiment the process is carried as a one-step fermentation process, i.e., simultaneous saccharification and fermentation. Examples of contemplated one-step fermentation processes, where adding of one or more antibacterial agents in accordance with the present invention is relevant, are described in, e.g., U.S. Pat. No. 4,316,956; WO 2003/066816. WO 2003/066826, WO 2004/081193, WO 2004/080923, WO 2005/008156, and WO2005/118795 (which are hereby incorporated by reference). In an embodiment alpha-amylase and/or carbohydrate-source generating enzyme(s), especially glucoamylase, is(are) used for hydrolyzing the uncooked starch-containing material to fermentable sugars. In a preferred embodiment the alpha-amylase is an acid alpha-amylase, preferably an acid fungal alpha-amylase. Contemplated enzymes and suitable concentrations are listed in the "Enzymes"-section below. The fermentation is preferably carried out in the presence of yeast, preferably a strain of *Saccharomyces*. Suitable fermenting organisms are listed in the "Fermenting Organisms"-section above. Examples of suitable antibacterial agents are listed in the section "Antibacterial Agents" above.

The antibacterial agent(s) may be added during saccharification before initiation of fermentation, Alternatively the antibacterial agent(s) may be added to the backset and/or thin stillage recycled to the fermentation step. In a preferred embodiment the antibacterial agent(s) is(are) left in contact with the fermentation medium for at least between 1 minute and 48 hours, preferably at least 1 hour, especially at least 24 hours before inoculation of the fermenting organism.

According to this aspect the process of the invention is carried out without gelatinization of the starch-containing material. The starch-containing material remains un-cooked. In one embodiment alpha-amylase and/or carbohydrate-source generating enzyme(s), preferably glucoamylase, is(are) present during saccharification and/or fermentation. According to the invention the desired fermentation product in question, such as ethanol, can be produced without liquefying the starch-containing material above gelatinizing temperatures.

The term "initial gelatinization temperature" means the lowest temperature at which gelatinization of the starch in question is initiated. Starch heated in water in general begins gelatinizing between 50° C. and 75° C.; the exact temperature of gelatinization depends on the specific starch, and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material is the temperature at which birefringence is lost in 5% of the starch granules using the method described by Gorinstein. S, and Lii. C., Starch/Stärke, Vol. 44 (12), pp. 461-466 (1992).

Before step (a) a slurry of starch-containing material, such as granular starch, having 20-55 wt.-% dry solids, preferably 25-40 wt.-% dry solids, more preferably 30-355% dry solids of starch-containing material may be prepared. The slurry may include water and/or process waters, such as backset and/or thin stillage, scrubber water, evaporator condensate or distillate, side stripper water from distillation, or other fermentation product plant process water. Because the process of this aspect of the invention the invention is carried out below the gelatinization temperature and thus no significant viscosity increase takes place, high levels of stillage may be used if desired. In an embodiment the aqueous slurry contains from about 1 to about 70 vol.-% stillage, preferably 15-60% vol.-% stillage, especially from about 30 to 50 vol.-% stillage.

The starch-containing material may be prepared by reducing the particle size, preferably by milling, to 0.05 to 3.0 mm, preferably 0.1-0.5 mm. After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids of the starch-containing material is converted into a soluble starch hydrolysate.

The process according to this aspect of the invention is conducted at temperatures below the initial gelatinization temperature. Preferably the temperature at which step (a) is carried out is between 30-75° C., preferably between 45-60° C.

In a preferred embodiment step (a) and step (b) are carried out as a simultaneous saccharification and fermentation process. In such preferred embodiment the process is typically carried at a temperature between 20-40° C., preferably 30-35° C., especially around 32° C. According to the invention the temperature may be adjusted up or down during fermentation.

In an embodiment simultaneous saccharification and fermentation is carried out so that the sugar level, such as glucose level, is kept at a low level such as below 6 wt.-%, preferably below about 3 wt.-%, preferably below about 2 wt.-%, more preferred below about 1 wt.-%, even more preferred below about 0.5%, or even more preferred 0.25% wt.-%, such as below about 0.1 wt.-%. Such low levels of sugar can be accomplished by simply employing adjusted quantities of enzyme and fermenting organism. At such low levels of sugar catabolic repression is avoided. A skilled person in the art can easily determine which quantities of enzyme and fermenting organism to use. The employed quantities of enzyme and fermenting organism may also be selected to maintain low concentrations of maltose in the fermentation broth. For instance, the maltose level may be kept below about 0.5 wt.-% or below about 0.2 wt.-%.

The process of the invention may be carried out at a pH in the range in the range between 4-7, preferably in the range between 5 and 6.

Enzymes

Alpha-Amylases

The alpha-amylase may according to the invention be of any origin. Preferred are alpha-amylases of fungal or bacterial origin.

In a preferred embodiment the alpha-amylase is an acid alpha-amylase, e.g., fungal acid alpha-amylase or bacterial acid alpha-amylase. The term "acid alpha-amylase" means an alpha-amylase (E.C. 3.2.1.1) which added in an effective amount has activity optimum at a pH in the range of 3 to 7, preferably from 3.5 to 6, or more preferably from 4-5.

Bacterial Alpha-Amylases

According to the invention a bacterial alpha-amylase may preferably be derived from the genus *Bacillus*.

In a preferred embodiment the *Bacillus* alpha-amylase is derived from a strain of *B. licheniformis, B. amyloliquefaciens, B. subtilis* or *B. stearothermophilus*, but may also be derived from other *Bacillus* sp. Specific examples of contemplated alpha-amylases include the *Bacillus licheniformis* alpha-amylase (BLA) shown in SEQ ID NO: 4 in WO 99/19467, the *Bacillus amyloliquefaciens* alpha-amylase (BAN) shown in SEQ ID NO: 5 in WO 99/19467, and the *Bacillus stearothermophilus* alpha-amylase (BSG) shown in SEQ ID NO: 3 in WO 99/19467. In an embodiment of the invention the alpha-amylase is an enzyme having a degree of identity of at least 60%, preferably at least 70%, more preferred at least 80%, even more preferred at least 90%, such as at least 95%, at least 96%, at least 97%, at least 93% or at least 99% identity to any of the sequences shown as SEQ ID NOS: 1, 2, 3, 4, or 5, respectively, in WO 99/19467.

The *Bacillus* alpha-amylase may also be a variant and/or hybrid, especially one described in any of WO 96/23873, WO 96/23874, WO 97/41213, WO 99/19467, WO 00/60059, and WO 02/10355 (all documents hereby incorporated by reference). Specifically contemplated alpha-amylase variants are disclosed in U.S. Pat. Nos. 6,093,562, 6,297,038 or U.S. Pat. No. 6,187,576 (hereby incorporated by reference) and include *Bacillus stearothermophilus* alpha-amylase (BSG alpha-amylase) variants having a deletion of one or two amino acid in position 179 to 182, preferably a double deletion disclosed in WO 1996/023873—see e.g., page 20, lines 1-10 (hereby incorporated by reference), preferably corresponding to delta (181-182) compared to the wildtype BSG alpha-amylase amino acid sequence set forth in SEQ ID NO:3 disclosed in WO 99/19467 or deletion of amino acids 179 and 180 using SEQ ID NO:3 in WO 99/19467 for numbering (which reference is hereby incorporated by reference). Even more preferred are Bacillus alpha-amylases, especially Bacillus stearothermophilus alpha-amylase, which have a double deletion corresponding to delta (181-182) and further comprise a N193F substitution (also denoted 1181*+G182*+ N193F) compared to the wild-type BSG alpha-amylase amino acid sequence set forth in SEQ ID NO: 3 disclosed in WO 99/19467.

The alpha-amylase may also be a maltogenic alpha-amylase. A "maltogenic alpha-amylase" (glucan 1,4-alpha-maltohydrolase, E.C. 3.2.1.133) is able to hydrolyze amylose and amylopectin to maltose in the alpha-configuration. A maltogenic alpha-amylase from Bacillus stearothermophilus strain NCIB 11837 is commercially available from Novozymes A/S, Denmark. The maltogenic alpha-amylase is described in U.S. Pat. Nos. 4,598,048, 4,604,355 and 6,162,628, which are hereby incorporated by reference.

Bacterial Hybrid Alpha-Amylases

A hybrid alpha-amylase specifically contemplated comprises 445 C-terminal amino acid residues of the Bacillus licheniformis alpha-amylase (shown as SEQ ID NO: 4 in WO 99/19467) and the 37 N-terminal amino acid residues of the alpha-amylase derived from Bacillus amyloliquefaciens (shown as SEQ ID NO: 3 in WO 99/194676), with one or more, especially all, of the following substitution:

G48A+T49I+G107A+H156Y+A181T+N190F+I201F+ A209V+Q264S (using the Bacillus licheniformis numbering). Also preferred are variants having one or more of the following mutations (or corresponding mutations in other Bacillus alpha-amylase backbones): H154Y, A181T, N190F, A209V and Q264S and/or deletion of two residues between positions 176 and 179, preferably deletion of E178 and G179 (using the SEQ ID NO: 5 numbering of WO 99/19467).

The bacterial alpha-amylase may be added in amounts as are well-known in the art. When measured in KNU units (described below in the "Materials & Methods"-section) the alpha-amylase activity is preferably present in an amount of 0.5-5,000 NU/g of DS, in an amount of 1-500 NU/g of DS, or more preferably in an amount of 5-1,000 NU/g of DS, such as 10-100 NU/g DS.

Fungal Alpha-Amylases

Fungal acid alpha-amylases include acid alpha-amylases derived from a strain of the genus Aspergillus, such as Aspergillus oryzae, Aspergillus niger, Aspergillus kawachii alpha-amylases.

A preferred acid fungal alpha-amylase is a Fungamyl-like alpha-amylase which is preferably derived from a strain of Aspergillus oryzae. In the present disclosure, the term "Fungamyl-like alpha-amylase" indicates an alpha-amylase which exhibits a high identity, i.e. more than 70%, more than 75%, more than 80%, more than 85% more than 90%, more than 95%, more than 96%, more than 97%, more than 98%, more than 99% or even 100% identity to the mature part of the amino acid sequence shown in SEQ ID NO: 10 in WO 96/23874.

Another preferred acid alpha-amylase is derived from a strain Aspergillus niger. In a preferred embodiment the acid fungal alpha-amylase is the one from Aspergillus niger disclosed as "AMYA_ASPNG" in the Swiss-prot/TeEMBL database under the primary accession no. P56271 and described in more detail in WO 89/01969 (Example 3). The acid Aspergillus niger acid alpha-amylase is also shown as SEQ ID NO: 1 in WO 2004/080923 (Novozymes) which is hereby incorporated by reference. Also variants of said acid fungal amylase having at least 70% identity, such as at least 80% or even at least 90% identity, such as at least 95%, at least 96%, at least 97%, at least 98%, or at least 99% identity to SEQ ID NO: 1 in WO 2004/080923 are contemplated. A suitable commercially available acid fungal alpha-amylase derived from Aspergillus niger is SP288 (available from Novozymes A/S, Denmark).

In a preferred embodiment the alpha-amylase is derived from Aspergillus kawachii and disclosed by Kaneko et al. J. Ferment. Bioeng. 81:292-298 (1996), "Molecular-cloning and determination of the nucleotide-sequence of a gene encoding an acid-stable alpha-amylase from Aspergillus kawachii"; and further as EMBL: #AB008370.

The fungal acid alpha-amylase may also be a wild-type enzyme comprising a carbohydrate-binding module (CBM) and an alpha-amylase catalytic domain (i.e., a none-hybrid), or a variant thereof. In an embodiment the wild-type acid alpha-amylase is derived from a strain of Aspergillus kawachii.

Fungal Hybrid Alpha-Amylases

In a preferred embodiment the fungal acid alpha-amylase is a hybrid alpha-amylase. Preferred examples of fungal hybrid alpha-amylases include the ones disclosed in WO 2005/003311 or U.S. Patent Application Publication no. 2005/0054071 (Novozymes) or U.S. patent application No. 60/638,614 (published as WO 2006/069290) which is hereby incorporated by reference. A hybrid alpha-amylase may comprise an alpha-amylase catalytic domain (CD) and a carbohydrate-binding domain/module (CBM), such as a starch binding domain, and optional a linker.

Specific examples of contemplated hybrid alpha-amylases include those disclosed in Tables 1 to 5 of the examples in co-pending U.S. patent application No. 60/638,614, including Fungamyl variant with catalytic domain JA118 and Athelia rolfsii SBD (SEQ ID NO: 100 in U.S. 60/638,614), Rhizomucor pusillus alpha-amylase with Athelia rolfsii AMG linker and SBD (SEQ ID NO: 101 in U.S. 60/638,614), Rhizomucor pusillus alpha-amylase with Aspergillus niger glucoamylase linker and SBD (which is disclosed in Table 5 as a combination of amino acid sequences SEQ ID NO: 20, SEQ ID NO: 72 and SEQ ID NO: 96 in U.S. application Ser. No. 11/316,535) or as V039 in Table 5 in WO 2006/069290, and Meripilus giganteus alpha-amylase with Athelia rolfsii glucoamylase linker and SBD (SEQ ID NO: 102 in U.S. 60/638, 614). Other specifically contemplated hybrid alpha-amylases are any of the ones listed in Tables 3, 4, 5, and 6 in Example 4 in U.S. application Ser. No. 11/316,535 or WO 2006/069290 (hereby incorporated by reference).

Other specific examples of contemplated hybrid alpha-amylases include those disclosed in U.S. Patent Application Publication no. 2005/0054071, including those disclosed in Table 3 on page 15, such as Aspergillus niger alpha-amylase with Aspergillus kawachii linker and starch binding domain.

Contemplated are also alpha-amylases which exhibit a high identity to any of above mention alpha-amylases, i.e., more than 70%, more than 75%, more than 80%, more than 85% more than 90%, more than 95%, more than 96%, more than 97%, more than 98%, more than 99% or even 100% identity to the mature enzyme sequences.

Commercial Alpha-Amylase Products

Preferred commercial compositions comprising alpha-amylase include MYCOLASE from DSM (Gist Brocades), BAN™, TERMAMYL™ SC, FUNGAMYL™, LIQUOZYME™ X and SAN™ SUPER, SAN™ EXTRA L (Novozymes A/S) and CLARASE™ L-40,000, DEX-LO™, SPEZYME™ FRED, SPEZYME™ AA, and SPEZYME™

DELTA AA (Genencor Int.), and the acid fungal alpha-amylase sold under the trade name SP288 (available from Novozymes A/S, Denmark).

An acid alpha-amylases may according to the invention be added in an amount of 0.1 to 10 AFAU/g DS, preferably 0.10 to 5 AFAU/g DS, especially 0.3 to 2 AFAU/g DS.

Carbohydrate-Source Generating Enzymes

The term "Carbohydrate-source generating enzyme" includes glucoamylase (being glucose generators), beta-amylase and maltogenic amylase (being maltose generators). A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrate may be converted directly or indirectly to the desired fermentation product, preferably ethanol. According to the invention a mixture of carbohydrate-source generating enzymes may be used. Especially contemplated mixtures are mixtures of at least a glucoamylase and an alpha-amylase, especially an acid amylase, even more preferred an acid fungal alpha-amylase. The ratio between acidic fungal alpha-amylase activity (AFAU) per glucoamylase activity (AGU) (AFAU per AGU) may in an embodiment of the invention be at least 0.1, in particular at least 0.16, such as in the range from 0.12 to 0.50 or more.

Glucoamylases

A glucoamylase used according to the invention may be derived from any suitable source, e.g., derived from a microorganism or a plant. Preferred glucoamylases are of fungal or bacterial origin, e.g., selected from the group consisting of *Aspergillus* glucoamylases, in particular *A. niger* G1 or G2 glucoamylase (Boel et al. (1984), EMBO J. 3 (5), p. 1097-1102), or variants thereof, such as one disclosed in WO 92/00381, WO 00/04136, WO 01/04273 and WO 03/029449 (from Novozymes, Denmark, hereby incorporated by reference); the *A. awamori* glucoamylase (WO 84/102921), *A. oryzae* (Agric. Biol. Chem. (1991), 55 (4), p. 941-949), or variants or fragments thereof.

Other *Aspergillus* glucoamylase variants include variants to enhance the thermal stability: G137A and G139A (Chen et al. (1996), Prot. Eng. 9, 499-505); D257E and D293E/Q (Chen et al. (1995), Prot. Engng. 8, 575-582); N182 (Chen et al. (1994), Biochem. J. 301, 275-281); disulphide bonds, A246C (Fierobe et al. (1996), Biochemistry, 35, 8698-8704; and introduction of Pro residues in position A435 and S436 (Li et al. (1997), Protein Engng. 10, 1199-1204. Other glucoamylases include *Athelia rolfsii* (previously denoted *Corticium rolfsii*) glucoamylase (see U.S. Pat. No. 4,727,026 and (Nagasaka, Y. et al. (1998) Purification and properties of the raw-starch-degrading glucoamylases from *Corticium rolfsii*, Appl Microbiol Biotechnol 50:323-330), *Talaromyces* glucoamylases, in particular, derived from *Talaromyces emersonii* (WO 99/28448). *Talaromyces leycettanus* (U.S. Pat. No. Re. 32,153), *Talaromyces duponti, Talaromyces thermophilus* (U.S. Pat. No. 4,587,215), or *Trametes cingulata* (WO 2006/069289). Bacterial glucoamylases contemplated include glucoamylases from the genus *Clostridium*, in particular *C. thermoamylolyticum* (EP 135,138), and *C. thermohydrosulfuricum* (WO 86/01831).

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U and AMG™ E (from Novozymes A/S); OPTIDEX™ 300 (from Genencor Int.); AMIGASE™ and AMIGASE™ PLUS (from DSM); G-ZYME™ G900, G-ZYME™ and G990 ZR (from Genencor Int.).

Glucoamylase may in an embodiment be added in an amount of 0.005-5 AGU/g DS, more preferably between 0.01-1 AGU/g DS, such as especially around 0.1-0.5 AG U/g DS.

Beta-Amylases

At least according to the invention the a beta-amylase (E.C 3.2.1.2) is the name traditionally given to exo-acting maltogenic amylases, which catalyze the hydrolysis of 1,4-alpha-glucosidic linkages in amylose, amylopectin and related glucose polymers. Maltose units are successively removed from the non-reducing chain ends in a step-wise manner until the molecule is degraded or, in the case of amylopectin, until a branch point is reached. The maltose released has the beta anomeric configuration, hence the name beta-amylase.

Beta-amylases have been isolated from various plants and microorganisms (W. M. Fogarty and C. T. Kelly, Progress in Industrial Microbiology, vol. 15, pp. 112-115, 1979). These beta-amylases are characterized by having optimum temperatures in the range from 40° C. to 65° C. and optimum pH in the range from 4.5 to 7. A commercially available beta-amylase from barley is NOVOZYM™ WBA from Novozymes A/S, Denmark and SPEZYME™ BBA 1500 from Genencor Int., USA.

Maltogenic Amylases

The amylase may also be a maltogenic alpha-amylase. A "maltogenic alpha-amylase" (glucan 114-alpha-maltohydrolase, E.G. 3.2.1.133) is able to hydrolyze amylose and amylopectin to maltose in the alpha-configuration. A maltogenic amylase from *Bacillus stearothermophilus* strain NCIB 11837 is commercially available from Novozymes A/S. Maltogenic alpha-amylases are described in U.S. Pat. Nos. 4,598, 048, 4,604,355 and 6,162.628, which are hereby incorporated by reference.

The maltogenic amylase may in a preferred embodiment be added in an amount of 0.05-5 mg total protein/gram DS or 0.05-5 MANU/g DS.

Use of Antibacterial Agents

In the final aspect the invention relates to the use of antibacterial agents for killing and/or inhibiting bacterial growth in fermentation product production processes.

The antibacterial agent is any of the ones mentioned in the "Antibacterial Agents" section above. Preferred are peptides, polypeptides, proteins and enzyme, preferably of bacterial or fungal origin or prepared synthetically.

Materials and Methods

Enzymes:

Bacterial Alpha-amylase A. *Bacillus stearothermophilus* alpha-amylase variant with the mutations: I181*+G182*+N193F disclosed in U.S. Pat. No. 6,187,576 and available on request from Novozymes A/S, Denmark.

Glucoamylase T: Glucoamylase derived from *Talaromyces emersonii* disclosed in WO1999/028448 and available from Novozymes A/S, Denmark.

Antibacterial Agents

Peptide A: Fungal defensin derived from the saprophytic ascomycete *Pseudoplectania nigrelia* also disclosed as amino acids 1-40 in SEQ ID NO:32 in WO 03/044049.

Peptide B: Synthetic peptide disclosed as SEQ ID NO:93 in WO 2005/105831.

Lysozyme from hen egg white, cat # L-7651, lot # 114K7054 purchased from Sigma.

Yeast:

RED STAR® available from Red Star/Lesaffre, USA

Bacteria:

Three of the *Lactobacillus* strains used in this study (*L. plantarum* #1, *L. paracasei* #2, *L. paracasei* #2a) were kindly donated by Professor Mike Ingledew (U, of Saskatchewan).
Media
CASO: Tryptic soy broth from BD Bacto Ref 211822
MRS agar (EMD Science, 1.10660.0500)
Equipment:
Spectrophotometer: Tecan Safire Austina, Serial No. 12901300079
Methods:

*Lactobacillus* Samples

The *Lactobacillus* strain (e.g., *L. plantarum* #1. *L. paracasei* #2, *L. paracasei* #2a) is stored as frozen culture until use. See J. Appl. Microbiol. 2001, 90, 819-28 for details. The culture is rehydrated in MRS broth (Difco) to initial cell concentrations of around $4 \times 10^7$. Samples are plated on MRS agar (EMD Science, 1.10660.0500) in an anaerobic environment for 2 days at 37° C. for colony counting.

Alpha-Amylase Activity (KNU)

The amylolytic activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e. at 37° C.+/−0.05; 0.0003 M $Ca^{2+}$; and pH 5.6) dextrinizes 5260 mg starch dry substance Merck Amylum solubile.

A folder EB-SM-0009.02/01 describing this analytical method in more detail is available upon request to Novozymes A/S, Denmark, which folder is hereby included by reference.

Determination of Acid-Alpha-Amylase-Activity (AFAU)

Acid alpha-amylase activity is measured in AFAU (Acid Fungal Alpha-amylase Units), which are determined relative to an enzyme standard.

The standard used is AMG 300 L (from Novozymes A/S, Denmark, glucoamylase wild-type *Aspergillus niger* G1, also disclosed in Boel et al., 1984, EMBO J. 3 (5): 1097-1102) and WO 92/00381). The neutral alpha-amylase in this AMG falls after storage at room temperature for 3 weeks from approx. 1 FAU/mL to below 0.05 FAU/mL.

The acid alpha-amylase activity in this AMG standard is determined in accordance with the following description. In this method, 1 AFAU is defined as the amount of enzyme, which degrades 5.260 mg starch dry matter per hour under standard conditions.

Iodine forms a blue complex with starch but not with its degradation products. The intensity of color is therefore directly proportional to the concentration of starch. Amylase activity is determined using reverse colorimetry as a reduction in the concentration of starch under specified analytic conditions.

| Starch + Iodine | Alpha-amylase<br>→<br>40° C., pH 2.5 | Dextrins + Oligosaccharides |
|---|---|---|
| Blue/violet | t = 23 sec. | Decoloration |

Standard conditions/reaction conditions: (per minute)

| | |
|---|---|
| Substrate: | Starch, approx. 0.17 g/L |
| Buffer: | Citate, approx. 0.03M |
| Iodine ($I_2$): | 0.03 g/L |
| $CaCl_2$: | 1.85 mM |

-continued

| | |
|---|---|
| pH: | 2.50 ± 0.05 |
| Incubation temperature: | 40° C. |
| Reaction time: | 23 seconds |
| Wavelength: | lambda = 590 nm |
| Enzyme concentration: | 0.025 AFAU/mL |
| Enzyme working range: | 0.01-0.04 AFAU/mL |

If further details are preferred these can be found in EB-SM-0259.02/01 available on request from Novozymes A/S Denmark, and incorporated by reference.

Acid Alpha-Amylase Units (AAU)

The acid alpha-amylase activity can be measured in AAU (Acid Alpha-amylase Units) which is an absolute method. One Acid Amylase Unit (AAU) is the quantity of enzyme converting 1 g of starch (100% of dry matter) per hour under standardized conditions into a product having a transmission at 620 nm after reaction with an iodine solution of known strength equal to the one of a color reference.

Standard conditions/reaction conditions:

| | |
|---|---|
| Substrate: | Soluble starch. Concentration approx. 20 g DS/L. |
| Buffer: | Citrate, approx. 0.13M, pH = 4.2 |
| Iodine solution: | 40.176 g potassium iodide + 0.088 g iodine/L |
| City water | 15°-20°dH (German degree hardness) |
| pH: | 4.2 |
| Incubation temperature: | 30° C. |
| Reaction time: | 11 minutes |
| Wavelength: | 620 nm |
| Enzyme concentration: | 0.13-0.19 AAU/mL |
| Enzyme working range: | 0.13-0.19 AAU/mL |

The starch should be Lintner starch, which is a thin-boiling starch used in the laboratory as colorimetric indicator. Lintner starch is obtained by dilute hydrochloric acid treatment of native starch so that it retains the ability to color blue with iodine. Further details can be found in EP 014041082, which disclosure is hereby included by reference.

Glucoamylase Activity (AGI)

Glucoamylase (equivalent to amyloglucosidase) converts starch into glucose. The amount of glucose is determined here by the glucose oxidase method for the activity determination. The method described in the section 76-11 Starch-Glucoamylase Method with Subsequent Measurement of Glucose with Glucose Oxidase in "Approved methods of the American Association of Cereal Chemists". Vol. 1-2 AACC, from American Association of Cereal Chemists, 2000; ISBN: 1-891127-12-8.

One glucoamylase unit (AGI) is the quantity of enzyme which will form 1 micromol of glucose per minute under the standard conditions of the method.

Standard conditions/reaction conditions:

| | |
|---|---|
| Substrate: | Soluble starch.<br>Concentration approx. 16 g dry matter/L. |
| Buffer: | Acetate, approx. 0.04M, pH = 4.3 |
| pH: | 4.3 |
| Incubation temperature: | 60° C. |
| Reaction time: | 15 minutes |
| Termination of the reaction: | NaOH to a concentration of approximately 0.2 g/L (pH~9) |
| Enzyme concentration: | 0.15-0.55 AAU/mL. |

The starch should be Lintner starch, which is a thin-boiling starch used in the laboratory as colorimetric indicator. Lintner starch is obtained by dilute hydrochloric acid treatment of native starch so that it retains the ability to color blue with iodine.

Glucoamylase Activity (AGU)

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used, Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: | acetate 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
|---|---|
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference.

Determination of Maltogenic Amylase Activity (MANU)

One MANU (Maltogenic Amylase Novo Unit) may be defined as the amount of enzyme required to release one micro mole of maltose per minute at a concentration of 10 mg of maltotriose (Sigma M 8378) substrate per ml of 0.1 M citrate buffer, pH 5.0 at 37° C. for 30 minutes.

EXAMPLES

Example 1

MIC Test for Two Antibacterial Peptides on Four *Lactobacillus* Cultures

Two antibacterial peptides (Peptide A and Peptide B) were tested using MIC test (Minimal Inhibitory Concentration).

Four different *Lactobacillus* cultures were prepared in CASO medium for 2 days at 37° C. under facultative anaerobic conditions. The four *Lactobacillus* cultures (*Lactobacillus paracasei* #2a, *Lactobacillus paracasei* #2, *Lactobacillus plantarum* #1 and *Lactobacillus fermentum* ATCC 14931) were mixed in equal volume. 190 microL bacterial culture was filled into microtiter plate wells (96 plate wells) and 10 microL of Peptide A and Peptide B, respectively, were added (total well volume was then 200 micros. Measurements were initiated. The microtiter plates were incubated with lids for 24 hours at 37° C. to secure optimal growth of facultative anaerobic lactobacilli strains. Peptide A and Peptide B were prepared from initial protein concentration of 4.27 mg protein/mL and 34.34 mg protein/mL respectively. The tested dosages were 0.5 to 60 micro grams peptide/ml for both peptides. All treatments were run in 8 replicates and the control (cells+media) were tested in 16 replicates.

Figure 2:
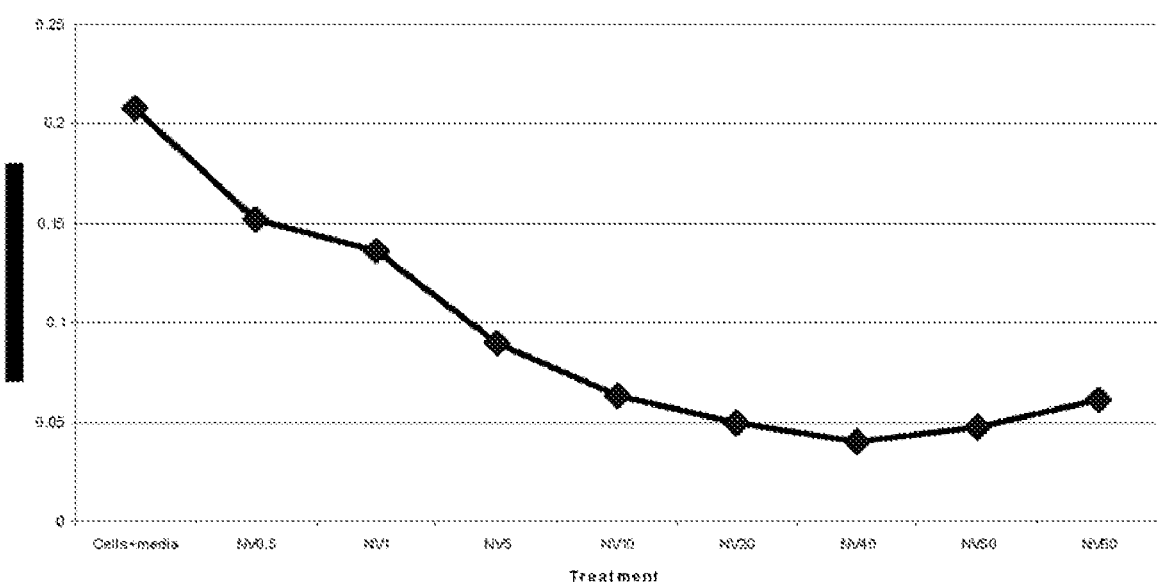
FIG. 2 shows the growth of mixture of four *Lactobacillus* strains over 24 hours at different concentrations of antibacterial Peptide B.

FIGS. 1 and 2 display the result of MIC test determined at 600 nm using a spectrophotometer.

Example 2

Antibacterial Effect of Peptide A in SSF

Milled corn was liquefied in an aqueous slurry (pH 5.6) using 50 NU/g DS Bacterial Alpha-Amylase A by heating until a temperature of 85° C. (approx 20 minutes) was reached. Thereafter the slurry is cooked for another 60 minutes.

The corn mash (CM) was split up into approximately 5 g of CM and added to 15 mL plastic centrifuge tubes. Fermentations were carried out as SSF at 32° C., 70 hours using RED STAR® yeast at a dosage around $1 \times 10^7$ Cells/ml of mash. Prior to the start of the fermentations, a 1/1/1 mixture of three *Lactobacillus* strains (*Lactobacillus paracasei* #2. *Lactobacillus paracasei* #2a, *Lactobacillus plantarum*) were added to some of the tubes containing the corn mash as indicated in Table 1 below and allowed to grow for 24 hours at 32° C. prior to pitching the yeast. The target initial total *Lactobacillus* cell count was $1 \times 10^7$ Cells/ml of mash, containing roughly equal cell counts of each strain. All tests were each run in 9 replicates and controls were included in the fermentation, The dry solid load was: 32.68 wt-%. The fermentations were monitored by weighing the individual tubes and recording the time and date of the measurement. The fermentation data was transferred to SAS JMP for conducting analysis of variance, test carried out using ($\alpha=0.05$).

| Treatment | Glucoamylase T AGU/g DS | Peptide A microgram/g DS | Lactobacillus |
|---|---|---|---|
| Control | 0.500 | | |
| PL 1 | 0.500 | 1 | + |
| PL 5 | 0.500 | 5 | + |
| PL 25 | 0.500 | 25 | + |
| Control_Lb | 0.500 | | + |

Figure 3:
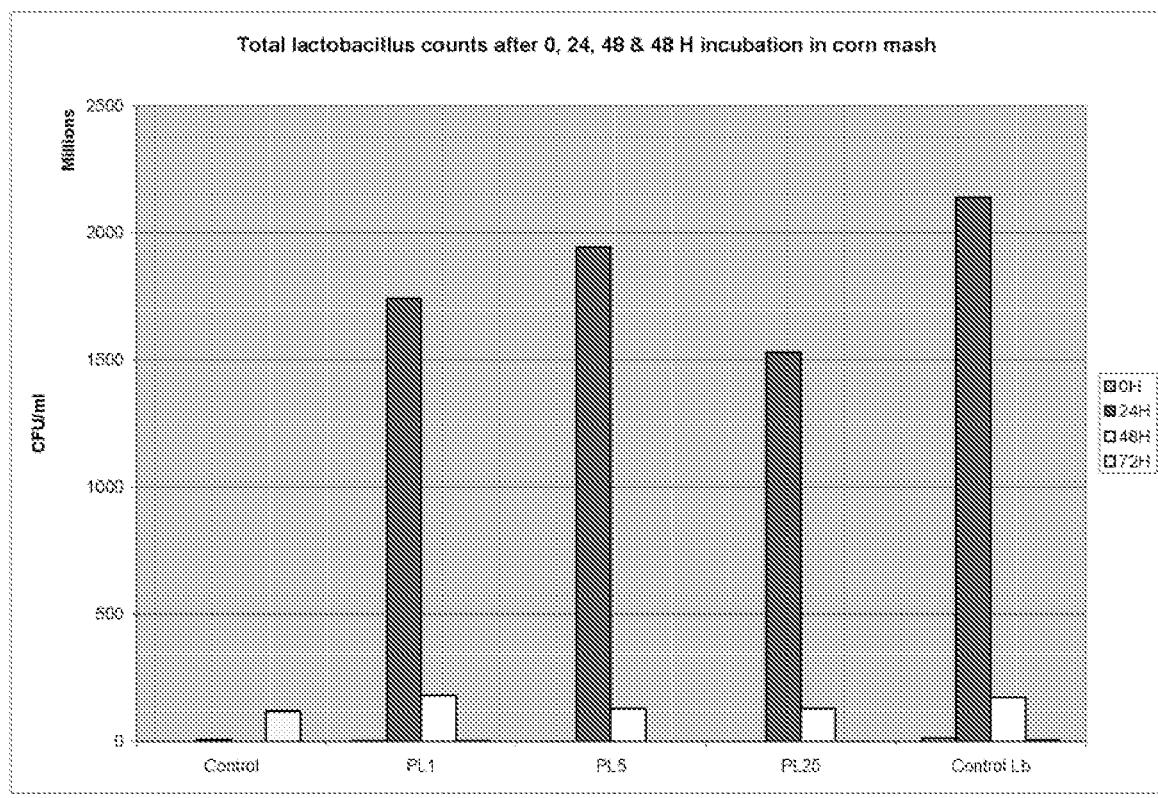
FIG. 3 shows the total count of Lactobacilli after 0, 24, 48, and 72 hours of SSF.

*Lactobacillus* strains were cultured in standard CASO broth/TSB, and incubated for two days in facultative anaerobic conditions at 37° C. *Lactobacillus* MRS Agar (EMD Science, 1.10660.0500) was used for plate counting. After plating 1 ml of the dilutions mentioned in Table 2 and displayed in FIG. 3, the plates were incubated in anaerobic conditions for 2 days at 37° C. The yeast counts were done by plating 1 ml of the dilutions mentioned in Table 5 on Yeast and Mold Petrifilm Plates (3M, 6407) and incubated for 2 days at 32.5° C.

TABLE 2

List of *Lactobacillus* counts over 3 days, Final counts (cfu/mL).

|  | 0 hours | 24 hours | 48 hours | 72 hours |
| --- | --- | --- | --- | --- |
| Control | 10000 | 9.1E+06 | 0.0E+00 | 1.2E+08 |
| PL1 | 1.8E+06 | 1.7E+09 | 1.8E+08 | 1.8E+06 |
| PL5 | 9.1E+05 | 1.9E+09 | 1.3E+08 | 6.4E+04 |
| PL25 | 9.1E+05 | 1.5E+09 | 1.3E+08 | 9.1E+05 |
| Control Lb | 1.4E+07 | 2.1E+09 | 1.7E+08 | 6.0E+06 |

Example 3

Effect of Lysozyme on *Lactobacillus* in Fermentation Medium

Milled corn was liquefied in an aqueous slurry (pH 5.6) using 50 NU/g DS Bacterial Alpha-Amylase A by heating until a temperature of 85° C. (approx 20 minutes) was reached. Thereafter the slurry is cooked for another 60 minutes. A sample of the liquefied corn mash (CM) was pH-adjusted to 5.05 with $H_2SO_4$. After pH adjustment, the mash was split up into approximately 59 of CM and added to 36 15 mL plastic centrifuge tubes. Various amounts of *L. paracasei* were then added to give an initial cell count of about $1-3 \times 10^6$/mL. Different dosages (0-100-300-1000 mg/L) of Lysozyme (Sigma) were also added to each tube. The tubes were then thoroughly vortexed and placed in a rack in 32° C. water bath. Tubes were pulled after 0, 24, and 48 hours for bacterial plating and counting. No additional Lysozyme was added to any of the tubes after time zero.

Figure 4:
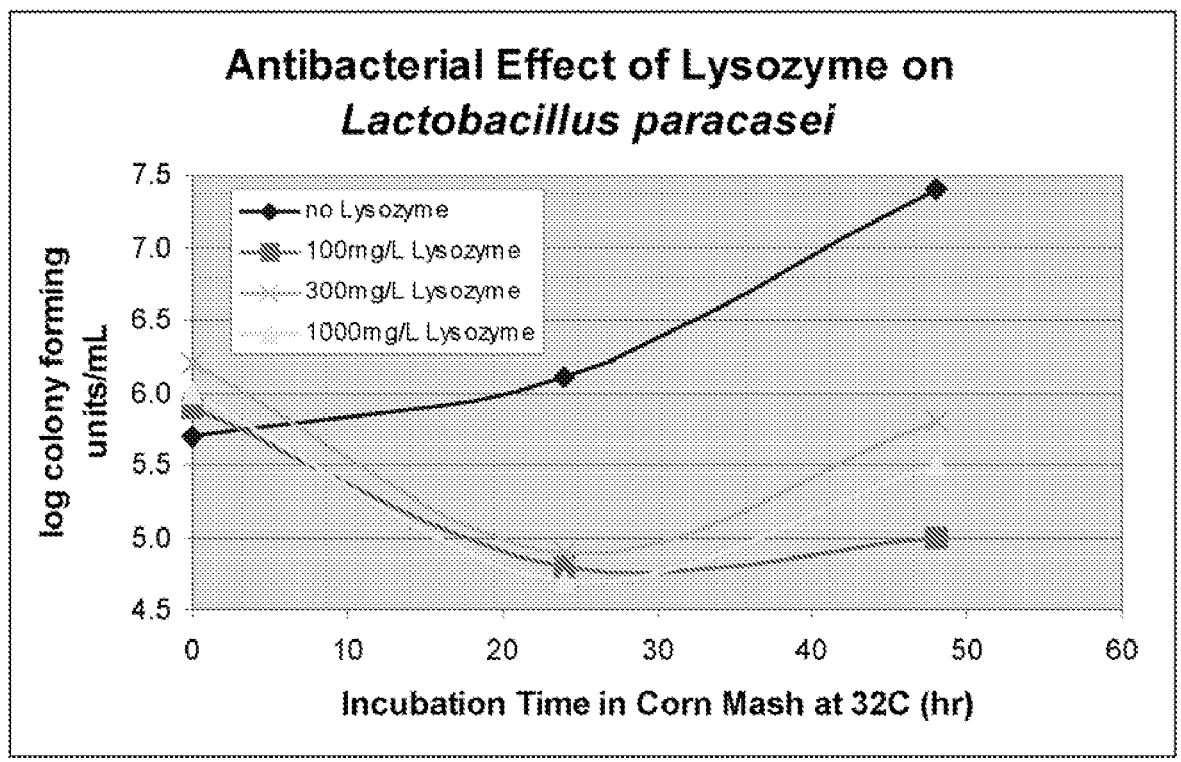
FIG. 4 shows the antibacterial effect of 0-1,000 mg Lysozyme/L fermentation medium on *Lactobacillus* over 48 hours.

FIG. 4 display the result of the test. The data suggests that Lysozyme is effective inhibiting growth of *Lactobacillus paracasei*.

The invention claimed is:

1. A process for producing a fermentation product, comprising:
   (a) liquefying a starch-containing material to form a liquefied starch;
   (b) saccharifying the liquefied starch using a carbohydrate source generating enzyme to form a sugar; and
   (c) fermenting the sugar using a fermenting organism under conditions suitable to produce the fermentation product, wherein one or more defensins are added before or during fermentation and wherein said one or more defensins are added at a concentration sufficient to inhibit growth of contaminating lactic acid bacterial cells.

2. The process of claim 1, wherein steps (b) and (c) are carried out sequentially or simultaneously.

3. The process of claim 1, wherein a slurry of the starch-containing material is heated to above the gelatinization temperature of the starch-containing material.

4. The process of claim 1, wherein the one or more defensins are added during liquefaction.

5. The process of claim 1, wherein the one or more defensins are added during saccharification.

6. The process of claim 1, wherein the one or more defensins are added during fermentation.

7. The process of claim 1, wherein the fermentation product is an alcohol.

8. The process of claim 7, wherein the alcohol is ethanol.

9. The process of claim 1, wherein the starch-containing starting material is whole grains, whole corn, or wheat grains.

10. The process of claim 1, wherein the liquefaction is carried out using an alpha-amylase.

11. The process of claim 1, wherein the bacterial cells are gram-positive bacteria or gram-negative bacteria cells.

12. The process of claim 11, wherein the bacterial cells are *Lactobacillus* cells.

13. A process for producing a fermentation product, comprising:
   (a) saccharifying a starch-containing material at a temperature below the initial gelatinization temperature of the starch-containing material to form a sugar; and
   (b) fermenting the sugar using a fermenting organism under conditions suitable to produce the fermentation product;

wherein one or more defensins are added before or during fermentation and wherein said one or more defensins are added at a concentration sufficient to inhibit growth of contaminating lactic acid bacterial cells that contaminate.

14. The process of claim 13, wherein the saccharification and fermentation are carried out sequentially or simultaneously.

15. The process of claim 13, wherein the fermentation is carried out at a temperature in the range from 20-40° C.

16. The process of claim 13, wherein the one or more defensins are added during saccharification.

17. The process of claim 13, wherein the bacterial cells are gram-positive bacteria or gram-negative bacteria cells.

18. The process of claim 17, wherein the bacterial cells are Lactobacillus cells.

19. The process of claim 13, wherein the starch-containing material is granular starch.

20. The process of claim 13, wherein the fermentation product is an alcohol.

21. The process of claim 20, wherein the alcohol is ethanol.

* * * * *